(12) United States Patent
Kim (10) Patent No.: US 11,134,856 B2
(45) Date of Patent: Oct. 5, 2021

(54) BIOMETRIC DATA MEASURING DEVICE

(71) Applicant: SUZHOU LEKIN SEMICONDUCTOR CO., LTD., Taicang (CN)

(72) Inventor: Chong Cook Kim, Seoul (KR)

(73) Assignee: SUZHOU LEKIN SEMICONDUCTOR CO., LTD., Taicang (CN)

(*) Notice: Subject to any disclaimer, the term of this patent is extended or adjusted under 35 U.S.C. 154(b) by 651 days.

(21) Appl. No.: 16/065,336

(22) PCT Filed: Dec. 21, 2016

(86) PCT No.: PCT/KR2016/014966
§ 371 (c)(1),
(2) Date: Jun. 22, 2018

(87) PCT Pub. No.: WO2017/111444
PCT Pub. Date: Jun. 29, 2017

(65) Prior Publication Data
US 2021/0161414 A1 Jun. 3, 2021

(30) Foreign Application Priority Data

Dec. 23, 2015 (KR) .................... 10-2015-0184717

(51) Int. Cl.
*A61B 1/00* (2006.01)
*A61B 5/024* (2006.01)

(52) U.S. Cl.
CPC .............................. *A61B 5/02427* (2013.01)

(58) Field of Classification Search
CPC .................................... A61B 1/00; A61N 1/00
See application file for complete search history.

(56) References Cited

FOREIGN PATENT DOCUMENTS

| JP | 2005-279255 | 10/2005 | |
|---|---|---|---|
| JP | 2005279255 A | * 10/2005 | ........... A61B 1/0684 |
| JP | 2013-208467 | 10/2013 | |
| JP | 2013208437 A | * 10/2013 | |
| JP | 2015-192139 | 11/2015 | |
| KR | 10-2013-0128527 | 11/2013 | |
| KR | 10-2014-0019509 | 2/2014 | |

OTHER PUBLICATIONS

International Search Report (with English Translation) and Written Opinion dated Mar. 30, 2017 issued in Application No. PCT/KR2016/014966.

* cited by examiner

*Primary Examiner* — Shirley Lu
(74) *Attorney, Agent, or Firm* — Birch, Stewart, Kolasch & Birch, LLP (57) ABSTRACT

A biometric data measurement device includes a light radiation unit configured to radiate green light having a full width at half maximum (FWHM) greater than or equal to 50 nm to a human body of a user; a light receiver configured to receive light reflected from or transmitted through the human body after being radiated from the light radiation unit; and a controller configured to calculate biometric data of the user using the received light wherein a lower wavelength limit of the FWHM is less than 500 nm, and an upper wavelength limit of the FWHM is greater than 520 nm.

20 Claims, 8 Drawing Sheets

BIOMETRIC DATA MEASURING DEVICE

CROSS-REFERENCE TO RELATED PATENT APPLICATIONS

This application is a U.S. National Stage Application under 35 U.S.C. § 371 of PCT Application No. PCT/KR2016/014966, filed Dec. 21, 2016, which claims priority to Korean Patent Application No. 10-2015-0184717, filed Dec. 23, 2015, whose entire disclosures are hereby incorporated by reference.

TECHNICAL FIELD

Embodiments relate to a biometric data measuring device.

BACKGROUND ART

With recent improvement in living standards and development of medical technology, the trend of population ageing has become predominant throughout the world. As the population ages, the incidence of chronic diseases is increasing. Increase in the elderly population living alone and people dying alone and abandoned due to decline of support from their family according to decrease in multi-generational households is becoming an important social issue.

Cases of chronic diseases such as hypertension, diabetes, cerebrovascular disease, and heart disease continue to increase. About half the occurrences of such diseases are caused by the behaviors of individuals or groups such as diet and exercise. Therefore, it is difficult to address these chronic diseases with a biomedical model of modern medicine alone, and a new disease control method, namely, a health promotion approach of eliminating health risk factors by improving lifestyle is required.

Care for the elderly who live alone is passively carried out through sensors for sensing the amount of activity or through home visits. In recent years, active care by measuring bio-signals such as heartbeats have emerged to care for health of the elderly living alone and prevent the elderly from dying alone and abandoned.

Personal-level kinesitherapy such as walking is widely performed as a way to prevent chronic diseases or as an alternative therapy. In such kinesitherapy, a pedometer or an exercise calorimeter is generally carried to check a target amount of exercise. Recently, a method of estimating the heart rate burden of a person during a workout by measuring the heart rate during exercise in real time has also been proposed.

The heart rate measurement method includes a piezoelectric technique using a piezoelectric element or the like, a magnetic technique using a magnetic tunneling junction (MTJ) element, a pressing technique using a film type pressure sensor, an impedance technique using bioelectrical impedance, and an optical technique using an optical sensor. Recently, a wristwatch type heart rate monitor wearable on the wrist or neck has been proposed.

In the case of conventional heart rate monitors, light is radiated to the blood vessels of a human body, and the heartbeat is measured using light that is transmitted through or reflected and received from the human body. However, in the conventional heart rate monitors, the body penetration rate and the receiving rate of the radiated light vary depending on race, sex, age, weight, or skin tissue, and therefore it may be difficult to accurately measure the heart rate.

DISCLOSURE

Technical Problem

Embodiments provide a biometric data measurement device capable of calculating accurate biometric data without being significantly affected by race, sex, age, weight, skin tissue, or the like.

Technical Solution

In one embodiment, a biometric data measurement device may include a light radiation unit configured to radiate green light having a full width at half maximum (FWHM) greater than or equal to 50 nm to a human body of a user, a light receiver configured to receive light reflected from or transmitted through the human body after being radiated from the light radiation unit, and a controller configured to calculate biometric data of the user using the received light.

For example, a lower wavelength limit of the FWHM may be less than 500 nm, and an upper wavelength limit of the FWHM may be greater than 520 nm.

For example, a wavelength range of the FWHM may include a wavelength of 520 nm.

For example, an intensity of the green light may have a pattern of repetition of a valley and a peak within the FWHM, wherein a minimum value of the valley may be greater than or equal to 80% of a maximum value of the peak.

For example, the light radiation unit may include a substrate, and a light emitting structure including a first conductivity-type semiconductor layer, an active layer, and a second conductivity-type semiconductor layer, the first conductivity-type semiconductor layer, the active layer and the second conductivity-type semiconductor being sequentially disposed on the substrate, wherein the active layer may include a plurality of well layers and a plurality of barrier layers, the plurality of well layers and the plurality of barrier layers being alternately arranged, wherein at least two lights emitted from at least two well layers of the plurality of well layers may have different wavelengths.

For example, the at least two well layers may include at least three well layers, wherein the at least three well layers may emit at least three lights having different wavelengths.

For example, the at least three lights may include first to third lights, wherein a range of a peak wavelength of one of the first to third lights may include 480 nm, a range of a peak wavelength of another one of the first to third lights may include 520 nm, and a range of a peak wavelength of the other one of the first to third lights may include 500 nm.

For example, the light radiation unit may further include an electron blocking layer disposed between the active layer and the second conductivity-type semiconductor layer.

For example, the at least two well layers may include a first well layer disposed between the electron blocking layer and the first conductivity-type semiconductor layer, a second well layer disposed between the first well layer and the first conductivity-type semiconductor layer, and a third well layer disposed between the second well layer and the first conductivity-type semiconductor layer, wherein the second or third well layer may have a smallest energy bandgap among the first to third well layers.

For example, a peak wavelength of a first light emitted from the first well layer may be between a peak wavelength of a second light emitted from the second well layer and a peak wavelength of a third light emitted from the third well layer.

For example, a wavelength of the first light emitted from the first well layer may be less than a wavelength of the second light emitted from the second well layer and a wavelength of the third light emitted from the third well layer.

For example, an energy bandgap of the second well layer may be larger than an energy bandgap of the third well layer.

For example, among the first to third well layers, the second well layer may have the smallest energy bandgap and the third well layer may have a largest energy bandgap.

For example, an energy bandgap of the third well layer may be larger than an energy bandgap of the second well layer.

For example, the electron blocking layer may have a doping concentration of 1×E17 atoms/cm$^3$ to 1×E22 atoms/cm$^3$.

For example, the biometric data measurement device may be wearable on a wrist of the user, and may further include a housing, the light radiation unit and the light receiver being arranged adjacent to each other in the housing.

For example, the controller may calculate a heart rate of the user using the received light.

For example, the light radiation unit may include a light source configured to emit light having an FWHM less than 50 nm, and a light conversion unit configured to convert the FWHM of the light emitted from the light source into 50 nm or more and then radiate the converted light to the human body as green light.

For example, the light conversion unit may generate the green light having an FWHM greater than or equal to 50 nm by converting a lower wavelength limit of and an upper wavelength limit of the FWHM of the light emitted from the light source, wherein the lower wavelength limit may be converted further than the upper wavelength limit.

For example, the light source and the light conversion unit may be integrated.

Advantageous Effects

A biometric data measurement device according to embodiments may measure biometric data, for example, heart rate, using green light having a wide full width at half maximum (FWHM), and therefore may accurately calculate the heart rate which is biometric data without being significantly influenced by race, sex, age, weight, or skin tone.

BEST MODE

Hereinafter, embodiments of the present disclosure will be described in detail with reference to the accompanying drawings in order to facilitate understanding of the present disclosure. However, the embodiments according to the present disclosure can be modified in various other forms, and the scope of the present disclosure should not be construed as being limited to the embodiments described below. The embodiments of the present disclosure are provided to enable those skilled in the art to more fully understand the present disclosure.

In the description of the embodiments, it is to be understood that, when an element is described as being "on" or "under" another element, the two elements may directly contact each other or may directly contact each other with one or more intervening elements present therebetween. Also, the term "on" or "under" may refer to not only an upward direction but also a downward direction with respect to one element.

It is also to be understood that relational terms, such as "first" and "second," on/upper portion/above and under/lower portion/below, are used only to distinguish between one subject or element and another subject or element without necessarily requiring or involving any physical or logical relationship or sequence between such subjects or elements.

Figure 1:
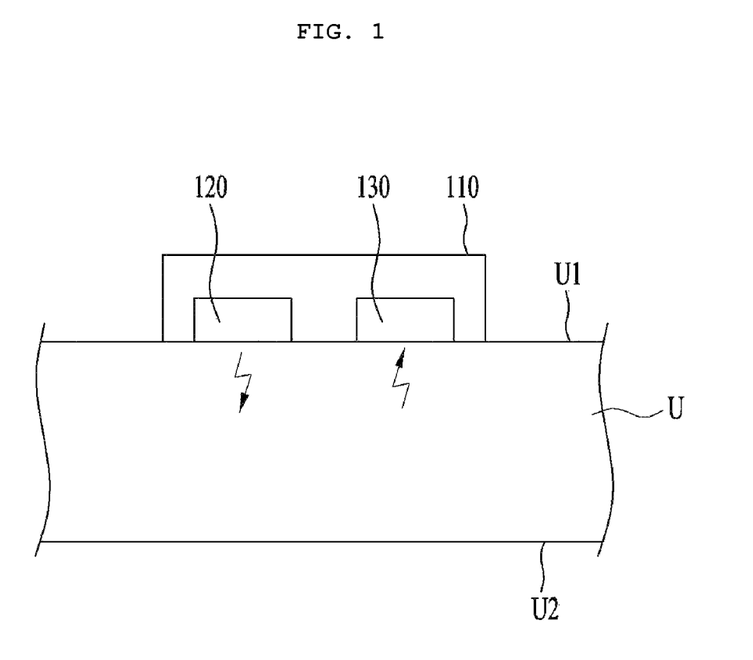
FIG. 1 is a cross-sectional view schematically showing a biometric data measurement device according to an embodiment coupled to the body of a user.
Figure 2:
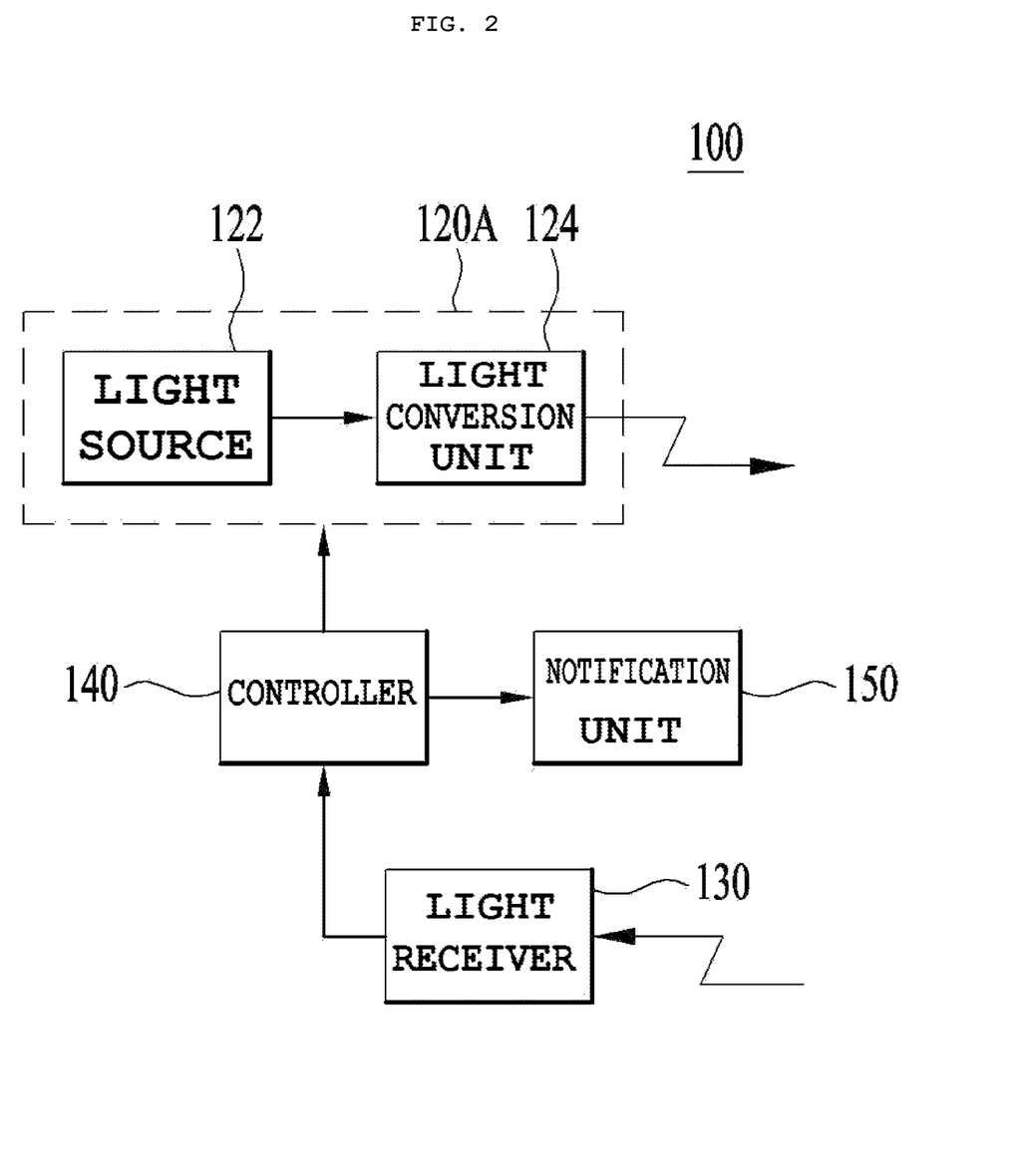
FIG. 2 is a block diagram of the biometric data measurement device according to an embodiment.

FIG. 1 is a cross-sectional view schematically showing a biometric data measurement device 100 according to an embodiment coupled to the human body U of a user. FIG. 2 is a block diagram of the biometric data measurement device 100 according to an embodiment.

Referring to FIGS. 1 and 2, the biometric data measurement device 100 according to an embodiment may include a housing 110, a light radiation unit 120 (120A), a light receiver 130, a controller 140, and a notification unit 150. For simplicity, the controller 140 and the notification unit 150 are omitted from FIG. 1, and the housing 110 is omitted from FIG. 2.

The light radiation unit 120 serves to radiate green light having a full width at half maximum (FWHM) of 50 nm or more to the human body U of a user.

Figure 3A:
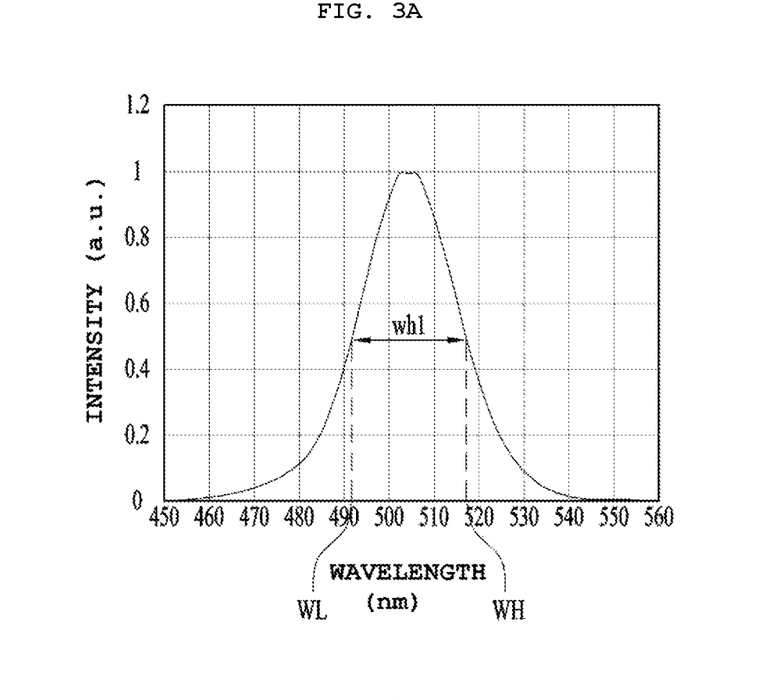
FIGS. 3A and 3B are graphs depicting light having a first FWHM and light having a second FWHM.
Figure 3B:
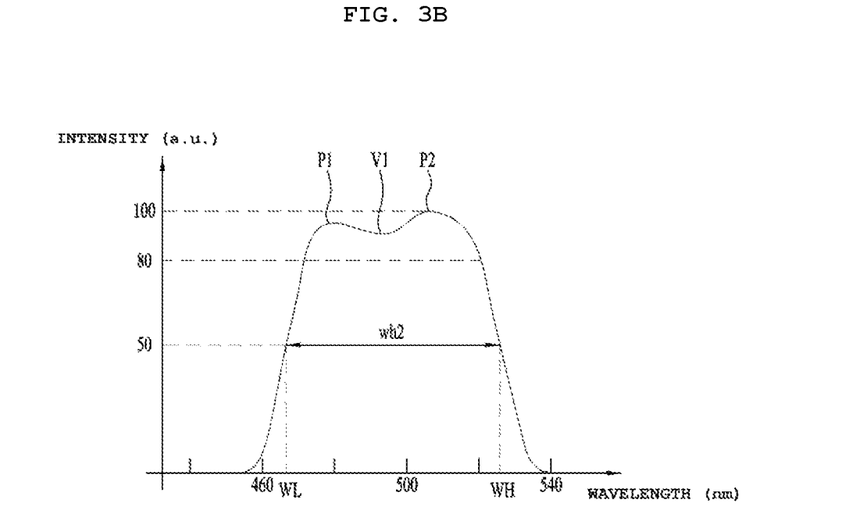

FIGS. 3A and 3B are graphs depicting light having a first FWHM wh1 and light having a second FWHM wh2. In each graph, the horizontal axis indicates wavelength and the vertical axis indicates the strength of light, that is, intensity. Particularly, FIG. 3B is a graph depicting the strength of light, that is, intensity in percent.

According to one embodiment, the light radiation unit 120 shown in FIG. 1 may be implemented as illustrated in FIG. 2. That is, the light radiation unit 120A shown in FIG. 2 corresponds to an embodiment of the light radiation unit 120 shown in FIG. 1. The light radiation unit 120A shown in FIG. 2 may include a light source 122 and a light conversion unit 124.

The light source 122 serves to emit light having the first FWHM wh1 less than 50 nm. For example, as shown in FIG. 3A, light having the first FWHM wh1 of 28 nm or less, which is less than 50 nm, may be emitted from the light source 122.

The light source 122 may be an LED chip, and embodiments are not limited to a specific form of the light source 122. The LED chip may be constituted by a blue LED chip or an ultraviolet LED chip, or may be a package including at least one of a red LED chip, a green LED chip, a blue LED chip, a yellow green LED chip or a white LED chip.

The white LED may be implemented by applying a yellow phosphor to a blue LED or using a red phosphor and a green phosphor together on a blue LED.

The light conversion unit 124 converts the first FWHM wh1 of the light emitted from the light source 122 into the second FWHM wh2 of 50 nm or more and then outputs the light having the FWHM of 50 nm or more to the human body U as green light. For example, the second half FWHM wh2 may be greater than or equal to 50 nm, as shown in FIG. 3B.

That is, referring to FIGS. 3A and 3B, the light conversion unit 124 adjusts the lower wavelength limit WL and the upper wavelength limit WH of the first FWHM wh1 in order to convert the first FWHM wh1 of light into the second FWHM wh2. In particular, the light conversion unit 124 adjusts the lower wavelength limit WL further than the upper wavelength limit WH, but embodiments are not limited thereto.

Figure 4:
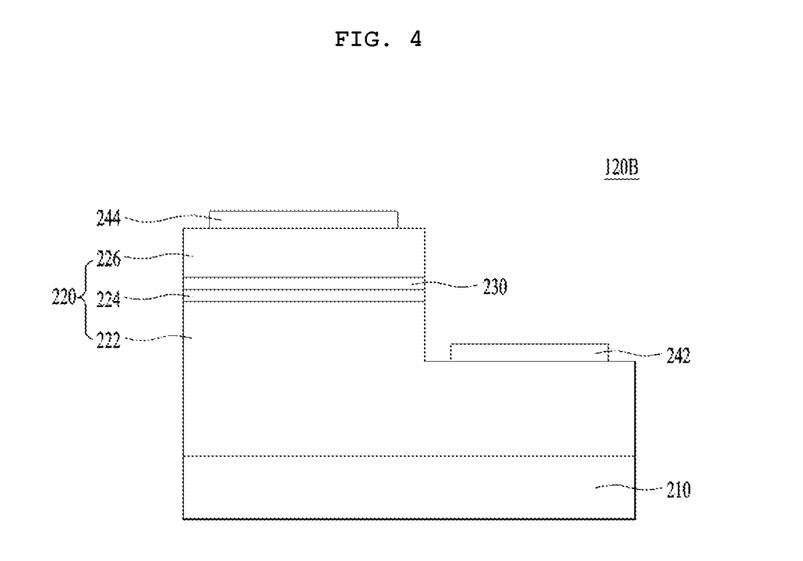
FIG. 4 is a cross-sectional view of another embodiment of a light radiation unit shown in FIG. 1.

FIG. 4 is a cross-sectional view of another embodiment 120B of the light radiation unit 120 shown in FIG. 1.

According to another embodiment, the light radiation unit 120B may emit light having the second FWHM wh2 of 50 nm or more, which is green light, and radiate the light to a human body. To this end, the light radiation unit 120B may include a light emitting element as shown in FIG. 4. That is, the green light having the second FWHM wh2 of 50 nm or more may be emitted from the light emitting element in itself. Specifically, the light radiation unit 120B shown in FIG. 4 corresponds to a case where the light source 122 and the light conversion unit 124 shown in FIG. 2 are integrated.

Although the light radiation unit 120B is illustrated in FIG. 4 as including a light emitting element having a horizontal bonding structure, embodiments are not limited to a specific bonding form of the light emitting element. That is, according to another embodiment, the light emitting element for implementing the light radiation unit 120B may have a vertical bonding structure or a flip chip bonding structure.

The light radiation unit 120B shown in FIG. 4 may include a substrate 210, a light emitting structure 220, and first and second electrodes 242 and 224.

The substrate 210 may include a conductive material or a non-conductive material. For example, the substrate 210 may include at least one of sapphire ($Al_2O_3$), GaN, SiC, ZnO, GaP, InP, $Ga_2O_3$, GaAs or Si.

For example, when the substrate 210 is a silicon substrate, it may have a (111) crystal face as a principal face. The silicon substrate may easily achieve a large diameter and have excellent thermal conductivity, but cracks may develop in the nitride-based emitting structure 220 due to the difference in coefficient of thermal expansion and lattice mismatch between the silicon and the nitride-based emitting structure 220. In order to prevent development of cracks, a buffer layer (or a transitional layer) (not shown) may be disposed between the substrate 210 and the light emitting structure 220. For example, the buffer layer may include, but is not limited to, at least one material selected from the group consisting of Al, In, N, and Ga. Further, the buffer layer may have a single layer structure or a multilayer structure.

The light emitting structure 220 is disposed on the substrate 210. The light emitting structure 220 may include a first conductivity-type semiconductor layer 222, an active layer 224, and a second conductivity-type semiconductor layer 226, which are sequentially disposed on the substrate 210.

The first conductivity-type semiconductor layer 222 is disposed on the substrate 210. The first conductivity-type semiconductor layer 222 may be formed of a semiconductor of a compound of groups III-V or groups II-VI doped with a first conductivity-type dopant. When the first conductivity-type semiconductor layer 222 is an n-type semiconductor layer, the first conductivity-type dopant may include Si, Ge, Sn, Se, and Te as n-type dopants, but is not limited thereto.

For example, the first conductivity-type semiconductor layer 222 may include a semiconductor material having a compositional formula of $Al_xIn_yGa_{(1-x-y)}N$ ($0 \leq x \leq 1$, $0 \leq y \leq 1$, $0 \leq x+y \leq 1$). The first conductivity-type semiconductor layer 222 may include one or more of GaN, InN, AlN, InGaN, AlGaN, InAlGaN, AlInN, AlGaAs, InGaAs, AlInGaAs, GaP, AlGaP, InGaP, AlInGaP or InP.

The active layer 224 may be disposed between the first conductivity-type semiconductor layer 222 and the second conductivity-type semiconductor layer 226. The active layer 224 is a layer that emits light having energy determined by an inherent energy band of a material constituting the active layer 224 when electrons (or holes) injected through the first conductivity-type semiconductor layer 222 and holes (or electrons) injected through the second conductivity-type semiconductor layer 226 meet each other.

The active layer 224 may be formed in at least one of a single well structure, a multi-well structure, a single quantum well structure, a multi-quantum well (MQW) structure, a quantum-wire structure, or a quantum dot structure.

The well layer/barrier layer of the active layer 224 may be formed of one or more pairs of InGaN/GaN, InGaN/InGaN, GaN/AlGaN, InAlGaN/GaN, GaAs(InGaAs)/AlGaAs, or GaP(InGaP)/AlGaP, but is not limited thereto. The well layer may be formed of a material having a bandgap energy lower than the bandgap energy of the barrier layer. That is, the active layer 224 may include a plurality of well layers and a plurality of barrier layers which are alternately arranged.

A conductive clad layer (not shown) may be formed on and/or under the active layer 224. The conductive clad layer may be formed of a semiconductor having a bandgap energy higher than the bandgap energy of the barrier layer of the active layer 224. For example, the conductive clad layer may include GaN, AlGaN, InAlGaN, or a superlattice structure. Further, the conductive clad layer may be doped with a n-type or p-type dopant.

The second conductivity-type semiconductor layer 226 may be disposed on the active layer 224. The second conductivity-type semiconductor layer 226 may be formed of a semiconductor compound and may be implemented by a compound semiconductor such as a group III-V compound semiconductor or a group II-VI compound semiconductor. For example, the second conductivity-type semiconductor layer 226 may include a semiconductor material having a compositional formula of $In_xAl_yGa_{1-x-y}N$ ($0 \leq x \leq 1$, $0 \leq y \leq 1$, $0 \leq x+y1$). The second conductivity-type semiconductor layer 226 may be doped with a second conductivity-type dopant. When the second conductivity-type semiconductor layer 226 is a p-type semiconductor layer, the second conductivity-type dopant may include Mg, Zn, Ca, Sr, and Ba as p-type dopants.

The first conductivity-type semiconductor layer 222 may be implemented as a p-type semiconductor layer, and the second conductivity-type semiconductor layer 226 may be implemented as an n-type semiconductor layer. Alternatively, the first conductivity-type semiconductor layer 222 may be implemented as an n-type semiconductor layer, and the second conductivity-type semiconductor layer 226 may be implemented as a p-type semiconductor layer.

The light emitting structure 220 may have one of an n-p junction structure, a p-n junction structure, an n-p-n junction structure and a p-n-p junction structure.

The light radiation unit 120B may further include an electron blocking layer (EBL) 230. The electron blocking layer 230 may be disposed between the active layer 224 and the second conductivity-type semiconductor layer 226. Since EBL 230 has a larger energy bandgap than the second conductivity-type semiconductor layer 226, electrons provided from the first conductivity-type semiconductor layer 222 may not be recombined in the active layer 224 and may be effectively prevented from overflowing to the second conductivity-type semiconductor layer 226. Therefore, the electron blocking layer 230 may improve the optical efficiency of the light radiation unit 120B by reducing the electrons consumed due to overflow.

In order to obtain an electron blocking effect, the EBL 230 should have a large energy bandgap and an appropriate thickness. As the electron blocking layer 230, a second conductive AlGaN or InAlGaN layer may be mainly used, but embodiments are not limited thereto.

In some cases, the EBL 230 may be omitted.

A first electrode 242 is disposed on the first conductivity-type semiconductor layer 222 exposed by performing mesa etching on the second conductivity-type semiconductor layer 226, the active layer 224, and a part of the first conductivity-type semiconductor layer 222. A second electrode 224 may be disposed on the second conductivity-type semiconductor layer 226. Each of the first and second electrodes 242 and 244 may include at least one of Al, Ti, Cr, Ni, Cu, or Au and may be formed have a single layer structure or a multilayer structure.

Hereinafter, the active layer 224 of the light radiation unit 120B shown in FIG. 4 that emits light having the second FWHM wh2 will be described.

Figure 5:
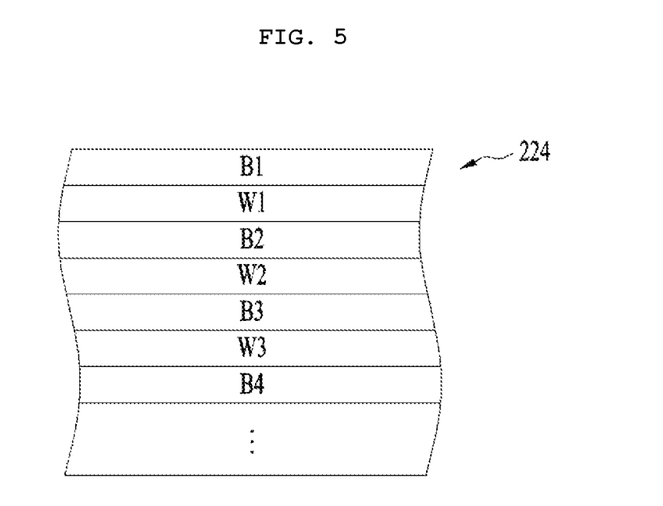
FIG. 5 is an enlarged cross-sectional view of an active layer shown in FIG. 4.

FIG. 5 is an enlarged cross-sectional view of the active layer 224 shown in FIG. 4.

Referring to FIG. 5, the active layer 224 may include barrier layers B1, B2, B3, B4, . . . and well layers W1, W2, W3, . . . , which are alternately arranged.

A first well layer is disposed between the EBL 230 and the first conductivity-type semiconductor layer 222, a second well layer is disposed between the first well layer and the first conductivity-type semiconductor layer 222, and a third well layer is disposed between the second well layer and the first conductivity-type semiconductor layer 222. That is, the first, second, and third well layers are disposed in this order such that the distance from the EBL 230 increases from the first well layer to the third well layer. Hereinafter, for simplicity, the first, second, and third well layers will be described as corresponding to W1, W2, and W3 shown in FIG. 5, respectively, but embodiments are not limited thereto. That is, the first well layer may be W1, the second well layer may be any one of W2 to W6, and the third well layer may be a layer other than the second well layer among W3 to W6 and may be disposed farther from the EBL 230 than the second well layer.

A first barrier layer B1 is disposed between the EBL 230 and the first well layer W1 and a second barrier layer B2 is disposed between the first well layer W1 and the second well layer W2. A third barrier layer B3 is disposed between the second well layer W2 and the third well layer W3 and a fourth barrier layer B4 is disposed between the third well layer W3 and the fourth well layer W4.

Hereinafter, it is assumed that light is emitted when a carrier trapped in the first well layer W1, W2, of the conduction band is recombined with a hole in the energy bandgap, rather than being emitted from the well layers W1, W2, . . . . However, for simplicity, this phenomenon will be expressed as "light is emitted from the well layer".

According to an embodiment, the wavelengths of at least two light rays respectively emitted from at least two well layers among the plurality of well layers W1, W2, may be different from each other. Thus, the second FWHM wh2 of the light emitted from the active layer 224 may be greater than or equal to 50 nm.

Figure 6A:
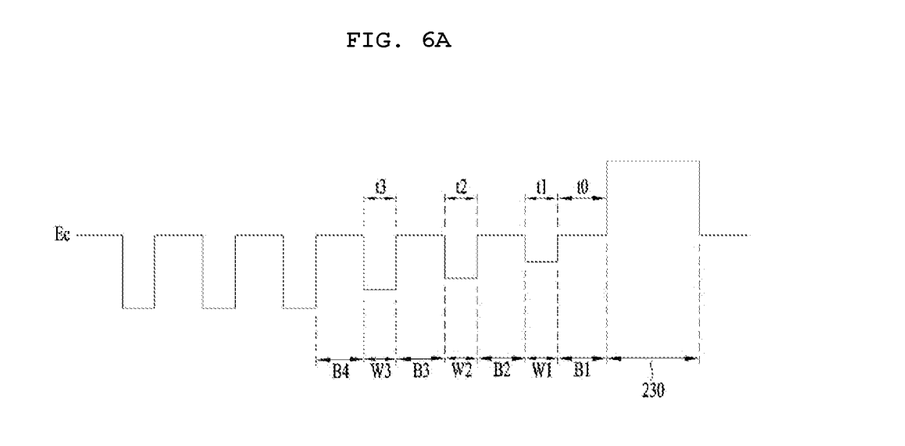
FIGS. 6A to 6C show an energy band diagram according to an embodiment of the active layer shown in FIG. 5.
Figure 6B:
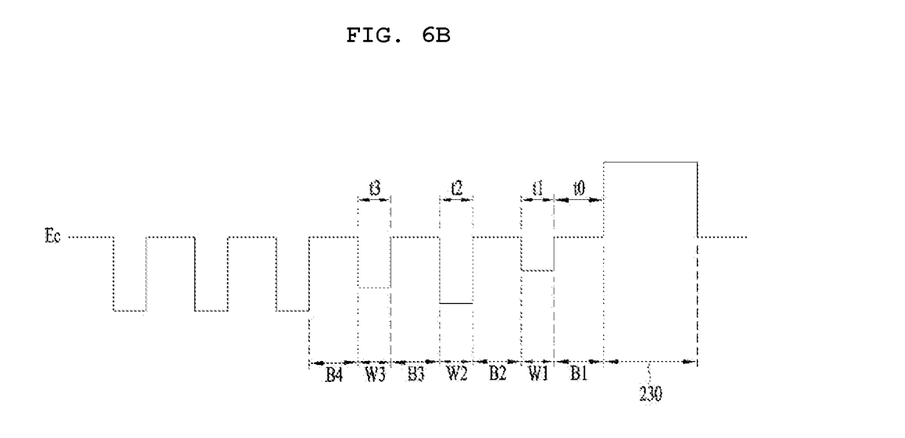
Figure 6C:
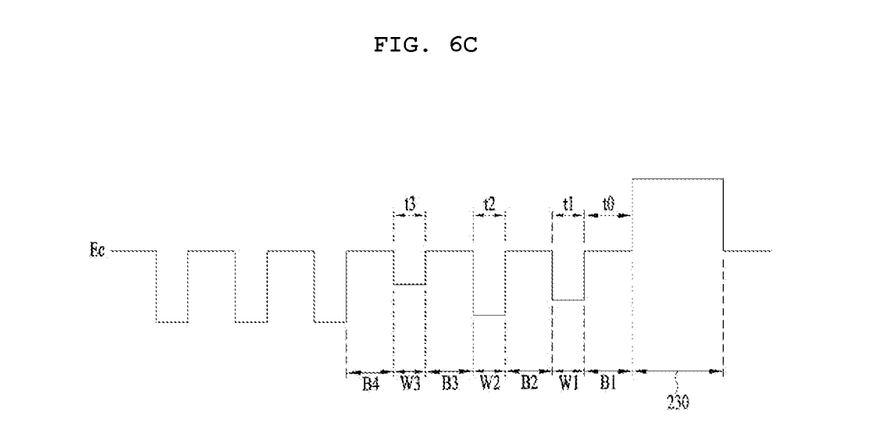

FIGS. 6A to 6C show an energy band according to an embodiment of the active layer 224 shown in FIG. 5. Here, Ec denotes a conduction band. Although not shown, a valence band Ev of the same shape is disposed under the conduction band Ec. The difference in level between the conduction band Ec and the valence band Ev is usually referred to as "bandgap energy".

Referring to FIGS. 6A to 6C, the wavelengths of the first to third lights L1, L2, and L3 emitted from the first to third well layers W1, W2 and W3, respectively, among the plurality of well layers W1, W2, may be different from each other.

According to an embodiment, a range of the peak wavelength of one of the first to third lights L1, L2, and L3 may include 480 nm, a range of the peak wavelength of another one of the first to third lights L1, L2 and L3 may include 520 nm, and a range of the peak wavelength of the other one of the first to third lights L1, L2 and L3 may include 500 nm.

When the first to third lights L1, L2, and L3 having wavelengths of 480 nm, 500 nm, and 520 nm are emitted from the first to third well layers W1, W2, and W3, respectively, as described above, the second FWHM wh2 of the light emitted from the active layer 224 may be greater than or equal to 50 nm.

Referring to FIG. 6A, a first light L1 having a peak wavelength of 480 nm may be emitted from the first well layer W1, a second light L2 having a peak wavelength of 500 nm may be emitted from the second well layer W2, and a third light L3 having a peak wavelength of 520 nm may be emitted from the third well layer W3. Thus, the energy bandgap of the second well layer W2 may be larger than the energy bandgap of the third well layer W3.

Referring to FIG. 6B, the first light L1 having a peak wavelength of 480 nm may be emitted from the first well layer W1, the second light L2 having a peak wavelength of 520 nm may be emitted from the second well layer W2, and the third light L3 having a peak wavelength of 500 nm may be emitted from the third well layer W3.

Figure 7:
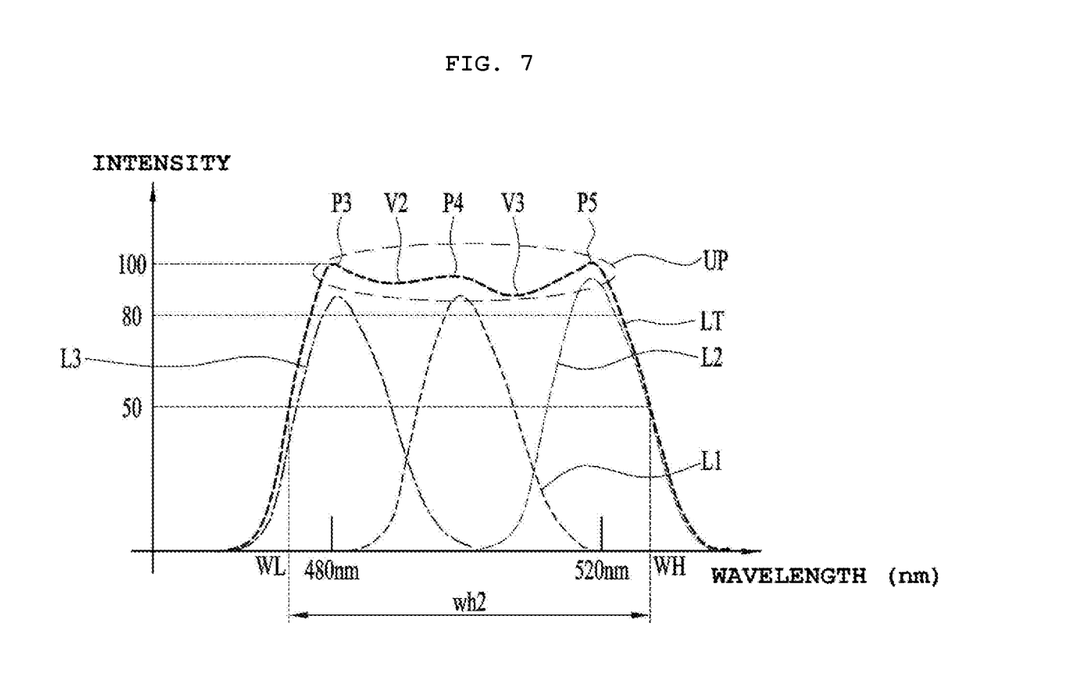
FIG. 7 is a graph depicting the intensities of light emitted from an active layer having a conduction band of a shape shown in FIG. 6C with respect to wavelength.

FIG. 7 is a graph depicting the intensities of light emitted from the active layer 224 having a conduction band Ec of a shape shown in FIG. 6C with respect to wavelength, wherein the horizontal axis indicates wavelength and the vertical axis indicates intensity. Particularly, FIG. 7 is a graph depicting the strength of light, that is, intensity, in percent.

Referring to FIGS. 6C and 7, a first light L1 having a peak wavelength of 500 nm may be emitted from the first well layer W1, a second light L2 having a peak wavelength of 520 nm may be emitted from the second well layer W2, and a third light L3 having a peak wavelength of 480 nm may be emitted from the third well layer W3. Thus, the peak wavelength of the first light L1 emitted from the first well layer W1 may be a median value of the peak wavelength of the second light L2 emitted from the second well layer W2 and the peak wavelength of the third light L3 emitted from the third well layer W3.

In addition, as shown in FIG. 6B or 6C, the energy bandgap of the third well layer W3 (or the energy level of the conduction band Ec) may be larger than the energy bandgap of the second well layer W2.

If holes are smoothly injected from the EBL 230 toward the position where the first well layer W1 is located, it is preferable that the wavelength of the first light L1 emitted from the first well layer W1 may be in about the middle of the wavelengths of the second light L2 and the third light L3, as shown in FIG. 6C. Therefore, in this case, the active layer 224 is formed to have an energy level profile as shown in FIG. 6C.

However, if holes are not smoothly injected from the EBL 230 toward the first well layer W1, the wavelength of the first light L1 emitted from the first well layer W1 is set to be lower than the wavelengths of the second and third lights L2 and L3, as shown in FIG. 6A. Then, the holes may smoothly move from the EBL 230 toward the first well layer W1.

The thickness t0 of the first barrier layer B1 disposed between the EBL 230 and the first well layer W1 may be reduced to ensure smooth injection of holes from the EBL 230 toward the first well layer W1.

In addition, in order to ensure smooth injection of holes from the EBL 230, the doping concentration and the doping efficiency of doping the EBL 230 with the second conductivity-type dopant such as, for example, Mg, should be high. For example, the doping concentration of the EBL 230 may be $1 \times E17$ atoms/cm$^3$ to $1 \times E22$ atoms/cm$^3$, but embodiments are not limited thereto.

As shown in FIGS. 6A to 6C, when the first, second and third lights L1, L2 and L3 having different peak wavelengths are emitted from the first, second and third well layers W1, W2, and W3, respectively, the second FWHM wh2 of light emitted from the active layer 224 may be greater than or equal to 50 nm. For example, when the first, second and third lights L1, L2 and L3 are emitted from the first to third well layers W1, W2, and W3, respectively as shown in FIG. 6C, light LT as shown in FIG. 7 may be emitted from the active layer 224.

Among the first to third well layers W1, W2 and W3 shown in FIGS. 6A to 6C, the energy bandgap of the first well layer W1 is not the lowest. In other words, the first well layer W1 is not the deepest. This is because, if the energy bandgap of the first well layer W1 is the lowest, it may be difficult for the holes to move to the second and third well layers W2 and W3, and thus most of the light is emitted from the first well layer W1 so that it may be difficult for the upper intensity portion UP of light radiated toward the human body U to have a flat shape. That is, as the energy bandgap of the first well layer W1 becomes larger (that is, as the depth of the first well layer W1 becomes shallower), the probability that holes move through the first well layer W1 to the second or third well layers W2, W3 may be increased. Therefore, the second or third well layer W2, W3 may have the smallest energy bandgap in place of the first well layer W1 among the first to third well layers W1, W2, W3. In order to flatten the upper intensity portion UP of the light LT shown in FIG. 7, the wavelength of the first light L1 may be adjusted.

In addition, to ensure smooth injection of holes from the EBL 230 toward the first well layer W1, the energy bandgap of the second well layer W2 may be set to be the smallest and the energy bandgap of the third well layer W3 may be set to be the largest, as shown in FIG. 6C. At this time, by adjusting the thickness of at least one of the first barrier layer B1, the second barrier layer B2, or the third barrier layer B3 to inject holes into the first to third well layers W1, W2, and W3 in a balanced manner, the upper intensity portion UP may have a flat shape.

If holes are not smoothly injected from the EBL 230 toward the first well layer W1, the energy bandgap of the second well layer W2 may be set to be larger than the energy bandgap of the third well layer W2, or the energy bandgap or the thickness of the barrier layers B1 to B3 may be reduced, as shown in FIG. 6A. Here, when the barrier layers B1 to B3 are implemented with InGaN, the energy bandgap of the barrier layers B1 to B3 may be reduced by increasing the composition of In.

As shown in FIGS. 6A to 6C described above, the first to third well layers W1, W2, and W3 have energy conduction bands Ec of various levels to emit a plurality of lights having different wavelengths. However, embodiments are not limited thereto. That is, a plurality of lights having different wavelengths may be generated using various methods. For example, when the first to third well layers W1, W2 and W3 include InGaN, the composition of In may be changed or the thicknesses t1, t2 and t3 of the first to third well layers W1, W2 and W3 may be adjusted such that a plurality of lights having different wavelengths may be emitted from the active layer 224.

Meanwhile, the lower wavelength limit WL of the FWHM of the light emitted from the light radiation unit 120, 120A, 120B may be less than 500 nm and the upper wavelength limit WH of the light emitted from the light radiation unit 120, 120A, 120B may be greater than 520 nm. For example, it may be seen from referring to FIG. 3B that the lower limit wavelength WL of the FWHM wh2 is approximately 465 nm and is thus less than 500 nm, and the upper wavelength limit WH of the FWHM wh2 is approximately 525 nm and is thus less than 520 nm. In addition, it may be seen from FIG. 7 that the lower wavelength limit WL of the FWHM wh2 is approximately 473 nm and is thus less than 500 nm, and the upper wavelength limit WH of the FWHM wh2 is approximately 526 nm and is thus greater than 520 nm.

Further, according to an embodiment, the wavelength range of the FWHM of light emitted from the light radiation unit 120, 120A, 120B may be determined to include a wavelength of 520 nm. For example, it may be seen from FIG. 3B that the wavelength range of the FWHM wh2 of light is between 465 nm and 525 nm, and the wavelength of 520 nm is included in this range. Further, it may be seen from FIG. 7 that the wavelength range of the FWHM wh2 of light is between 473 nm and 526 nm, and the wavelength of 520 nm is included in this range.

In addition, according to an embodiment, the intensity of the green light within the FWHM of light emitted from the light radiation unit 120, 120A, 120B may have a pattern in which the valley and the peak are repeated. For example, referring to FIG. 3B, the intensity of light within the FWHM wh2 may have a pattern in which a valley V1 and peaks P1 and P2 are repeated. In addition, referring to FIG. 7, the intensity of the light within the FWHM wh2 may have a pattern in which the valleys V2 and V3 and the peaks P3, P4 and P5 are repeated.

In addition, the least value of the valleys may be greater than or equal to 80% of the greatest value of the peaks. For example, it may be seen from FIG. 3B that the least value of the valley V1 is greater than or equal to 80% of the greatest value P2 of the peaks P1 and P2. In addition, it may be seen from FIG. 7 that the least value V3 of the valleys V2 and V3 is greater than or equal to 80% of the greatest value P3 or P5 of the peaks P3, P4 and P5.

In addition, the difference in intensity between the valleys and the peaks may be within 10%. For example, referring to FIG. 3B, the difference in intensity between the valley V1 and the peaks P1 and P2 may be within 10% of the maximum value (100%) of the light intensity. As deviation of the upper strength level decreases within the FWHM wh2, the intensity profile of the light may become flatter.

The light receiver 130 serves to receive light reflected by or transmitted through the human body U after being radiated from the light radiation unit 120, 120A, 120B. That is, the light receiver 130 may be implemented by a kind of photodiode.

The controller 140 calculates the biometric data of a user using the light received by the light receiver 130, and outputs the calculated biometric data. Here, the biometric data may be, for example, the user's heart rate (or pulse rate), but embodiments are not limited thereto.

Figure 8:
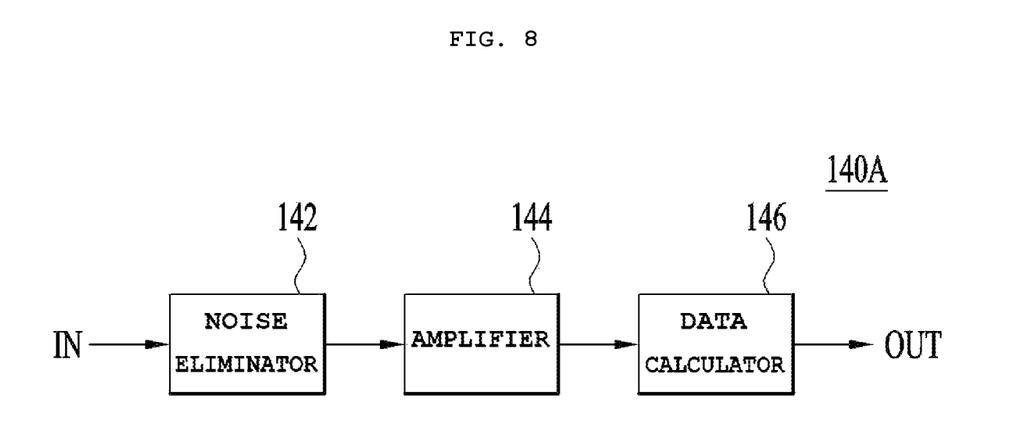
FIG. 8 is a block diagram according to an embodiment of a controller shown in FIG. 2.

FIG. 8 is a block diagram according to an embodiment 140A of the controller 140 shown in FIG. 2, which may include a noise eliminator 142, an amplifier 144, and a data calculator 146.

Referring to FIG. 8, the noise eliminator 142 cuts, as measured data, a wavelength band that sensitively changes in the light received through an input terminal IN after being reflected by or transmitted through the human body U, eliminate noise from the cut data and output a noise-eliminated result to the amplifier 144.

Here, when the biometric data to be calculated by the controller 140, 140A corresponds to the user's heart rate, the light received by the noise eliminator 142 may be a photoplethysmography (PPG) signal.

The pressure created by the heartbeat causes a flow of blood in the blood vessel. Every time this heartbeat occurs, the pressure acts on the terminal capillaries of the body, including the fingers, toes, and earlobes. The arterial blood in the terminal capillaries of the body feeds blood into cell tissues and returns to the heart through the vein. Thus, whenever a heartbeat takes place, increase and decrease of the amount of arterial blood is repeated in the blood vessels at the terminals of the body.

When light is radiated to the human body U from the light radiation unit 120, 120A, 120B, light is absorbed in the blood, bones and tissues, and part of the light is transmitted through the human body U or reflected from the human body U and reaches the light receiver 130. The light having an amount reduced by the amount of light absorbed by the human body U is received and detected by the light receiver 130. Therefore, a change in the amount of light received by the light receiver 130 reflects a change in blood flow. As such, by measuring the light amount of the light detected by the light receiver 130, a change in blood flow synchronized with the heartbeat may be detected. That is, the optical signal received by the light receiver 130 is a change in the blood flow volume according to the heartbeat and may be called a "pulse wave".

Therefore, the above-described embodiment of extracting biometric data using the light received by the light receiver 130 may be applied to various fields such as electroencephalography (EEG), electrocardiography (ECG), electromyography (EMG), photoplethysmography (PPG), respiration, and electrooculography (EOG).

Generally, the PPG signal may be activated in a predetermined frequency band, for example, a band of 0.04 Hz to 0.4 Hz. As the noise eliminator 142, a low-pass filter, a band-pass filter, or the like may be used in order to remove noise occurring outside the active frequency band.

The noise eliminator 142 may function to eliminate noise in various frequency bands such as noise caused by noise of an electric signal, noise caused by the bio-potential occurring in the human body U, and noise caused by user movement. However, embodiments are not limited to the kinds of noise eliminated by the noise eliminator 142.

The amplifier 144 amplifies a noise-eliminated result obtained by the noise eliminator 142 and outputs the amplified result to the data calculator 146. The level of the signal of the noise-eliminated result may be weak. Accordingly, the amplifier 144 serves to amplify the weak level of the signal. Therefore, the amplifier 144 may be omitted if the signal level of the noise-eliminated result is not weak.

The data calculator 146 may calculate the biometric data of the user using the amplified result obtained by the amplifier 144 and output the calculated biometric data through an output terminal OUT.

In addition, the controller 140 may control light emission of the light radiation unit 120, 120A, 120B or light reception of the light receiver 130. That is, the light radiation unit 120, 120A, 120B may emit light under control of the controller 140. Further, the light receiver 130 may receive light reflected from the human body U under control of the controller 140.

Referring back to FIG. 2, the notification unit 150 may notify the user of the biometric data calculated by the controller 140 in at least one of a visual manner or an audible manner.

In addition, the biometric data calculated by the controller 140 may be provided not only to the user but also to medical staff located at a remote distance. For this purpose, the notification unit 150 may include a communication unit (not shown) configured to transmit the calculated biometric data to the medical staff located at a remote distance.

Referring back to FIG. 1, the housing 110 may have a shape that is wearable on the user's wrist or the like and may accommodate the light radiation unit 120, 120A, 120B and the light receiver 130, which are disposed adjacent to each other. The housing 110 may be a kind of belt, but embodiments are not limited to a specific form of the housing 110.

In the example of FIG. 1, the light radiation unit 120, 120A, 120B and the light receiver 130 are arranged side by side on the same surface U1 of the human body U. This is intended to allow the light receiver 130 to receive light reflected from the human body U. However, according to another embodiment, when the light receiver 130 is to receive light transmitted through the human body U, the light radiation unit 120, 120A, 120B may be disposed on a first surface U1 of the human body U and the light receiver 130 may be disposed on a second surface U2 opposite to the first surface U1. In this case, the housing 110 may have a shape suitable to accommodate both the light radiation unit 120, 120A, 20B and the light receiver 130 disposed on the first and second surfaces U1 and U2, respectively.

When light is projected onto the human body U to measure the biometric data of the human body U, for example, the heart rate, and the heart rate is measured using light reflected from the human body U or light transmitted through the human body U, the sensitivity of the light projected onto the human body U may vary depending on the race, sex, age, body weight, or skin tissue.

Figure 9A:
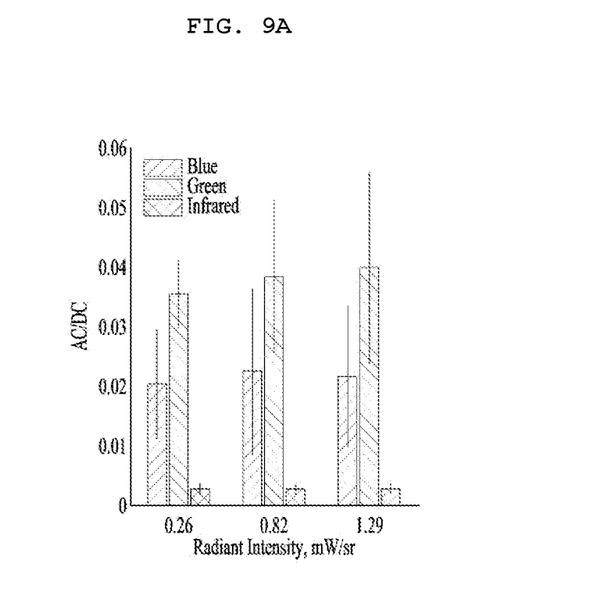
FIGS. 9A and 9B are graphs depicting the AC/DC ratio of parts of the human body as a function of intensity.
Figure 9B:
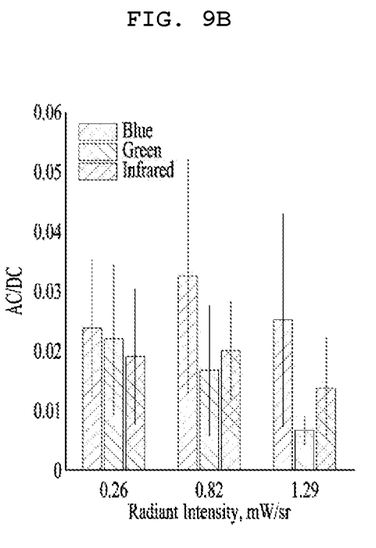

FIGS. 9A and 9B are graphs depicting the AC/DC ratio of parts of a human body as a function of intensity. Here, the AC/DC ratio represents the ratio of the AC component (AC) to the DC component (DC) of the intensity of light.

As shown in FIG. 9A, when light is radiated onto the wrist, the AC/DC ratio of the green light is relatively high.

On the other hand, as shown in FIG. 9B, when light is radiated onto the forehead, the AC/DC ratio of the blue light is relatively high. This is because the skin depth at which the change in blood flow is measurable varies according to the parts of the human body subjected to measurement.

Taking this into consideration, the biometric data measurement device 100 according to an embodiment measures biometric data using green light having a wide FWHM of 50 nm or more. Green light has a wide wavelength band. Therefore, with the green light, biometric data may be accurately calculated without being greatly affected by race, sex, age, body weight or skin tissue.

While the present disclosure has been particularly shown and described with reference to exemplary embodiments thereof, it is to be understood that the disclosure is not limited to the disclosed embodiments. It will be understood by those skilled in the art that various modifications and applications are possible without departing from the essential features of the embodiments. For example, each component specifically shown in the embodiments may be modified and implemented. It is to be understood that all changes and modifications that come within the meaning and range of equivalency of the claims are therefore intended to be embraced therein.

MODE FOR INVENTION

The mode for carrying out the disclosure has been fully described in the "Best Mode".

INDUSTRIAL APPLICABILITY

The biometric data measurement device according to embodiments may be applicable to various fields such as electroencephalography (EEG), electrocardiography (ECG), electromyography (EMG), photoplethysmography (PPG), respiration, and electrooculography (EOG).

The invention claimed is:

1. A biometric data measurement device, comprising:
a light radiation unit configured to radiate green light having a full width at half maximum (FWHM) greater than or equal to 50 nm to a human body of a user;
a light receiver configured to receive light reflected from or transmitted through the human body after being radiated from the light radiation unit; and
a controller configured to calculate biometric data of the user using the received light
wherein a lower wavelength limit of the FWHM is less than 500 nm, and an upper wavelength limit of the FWHM is greater than 520 nm,
wherein an intensity of the green light has a pattern of repetition of a valley and a peak within the FWHM, and
wherein a minimum value of the valley is greater than or equal to 80% of a maximum value of the peak.

2. The biometric data measurement device according to claim 1, wherein the light radiation unit comprises:
a substrate; and
a light emitting structure comprising a first conductivity-type semiconductor layer, an active layer, and a second conductivity-type semiconductor layer, the first conductivity-type semiconductor layer, the active layer and the second conductivity-type semiconductor being sequentially disposed on the substrate,
wherein the active layer comprises a plurality of well layers and a plurality of barrier layers, the plurality of well layers and the plurality of barrier layers being alternately arranged,
wherein at least two lights emitted from at least two well layers of the plurality of well layers have different wavelengths.

3. The biometric data measurement device according to claim 2, wherein the at least two well layers comprise at least three well layers,
wherein the at least three well layers emit at least three lights having different wavelengths, the at least three lights comprising first to third lights,
wherein: a range of a peak wavelength of one of the first to third lights comprises 480 nm;
a range of a peak wavelength of another one of the first to third lights comprises 520 nm; and
a range of a peak wavelength of the other one of the first to third lights comprises 500 nm.

4. The biometric data measurement device according to claim 2, wherein the light radiation unit further comprises:
an electron blocking layer disposed between the active layer and the second conductivity-type semiconductor layer,
wherein the at least two well layers comprises:
a first well layer disposed between the electron blocking layer and the first conductivity-type semiconductor layer;
a second well layer disposed between the first well layer and the first conductivity-type semiconductor layer; and
a third well layer disposed between the second well layer and the first conductivity-type semiconductor layer,
wherein the second or third well layer has a smallest energy bandgap among the first to third well layers.

5. The biometric data measurement device according to claim 4, wherein a peak wavelength of a first light emitted from the first well layer is between a peak wavelength of a second light emitted from the second well layer and a peak wavelength of a third light emitted from the third well layer, and
wherein a wavelength of the first light emitted from the first well layer is less than a wavelength of the second light emitted from the second well layer and a wavelength of the third light emitted from the third well layer.

6. The biometric data measurement device according to claim 4, wherein an energy bandgap of the second well layer is larger than an energy bandgap of the third well layer.

7. The biometric data measurement device according to claim 4, wherein, among the first to third well layers, the second well layer has the smallest energy bandgap and the third well layer has a largest energy bandgap.

8. The biometric data measurement device according to claim 4, wherein an energy bandgap of the third well layer is larger than an energy bandgap of the second well layer.

9. The biometric data measurement device according to claim 1, further comprising:
a housing, the light radiation unit and the light receiver being arranged adjacent to each other in the housing.

10. The biometric data measurement device according to claim 1, wherein the light radiation unit comprises:
a light source configured to emit light having an FWHM less than 50 nm; and
a light conversion unit configured to convert the FWHM of the light emitted from the light source into 50 nm or more and then radiate the converted light to the human body as green light.

11. The biometric data measurement device according to claim 10, wherein the light conversion unit generates the green light having an FWHM greater than or equal to 50 nm by converting a lower wavelength limit of and an upper wavelength limit of the FWHM of the light emitted from the light source, wherein the lower wavelength limit is converted further than the upper wavelength limit.

12. The biometric data measurement device according to claim 5, wherein the electron blocking layer has a doping concentration of $1 \times E17$ atoms/cm$^3$ to $1 \times E22$ atoms/cm$^3$.

13. The biometric data measurement device according to claim 9, wherein the housing is wearable on a wrist of the user.

14. The biometric data measurement device according to claim 9, wherein the controller calculates a heart rate of the user using the received light.

15. The biometric data measurement device according to claim 10, wherein the light source and the light conversion unit are integrated.

16. The biometric data measurement device according to claim 1, wherein a upper intensity portion of the green light radiated from the light radiation unit toward the human body has a flat shape.

17. The biometric data measurement device according to claim 2, wherein the plurality of the well layers includes InGaN.

18. The biometric data measurement device according to claim 1, wherein a wavelength range of the FWHM is between 473 nm and 526 nm.

19. The biometric data measurement device according to claim 18, wherein the wavelength range of the FWHM includes 520 nm.

20. The biometric data measurement device according to claim 1, wherein a difference in intensity between the valleys and the peaks is within 10%.

* * * * *